United States Patent
Ahluwalia et al.

(10) Patent No.: US 6,239,170 B1
(45) Date of Patent: May 29, 2001

(54) INHIBITION OF HAIR GROWTH

(76) Inventors: Gurpreet S. Ahluwalia, 8632 Stable View CT., Gaithersburg, MD (US) 20879; Douglas Shander, 16112 Howard Landing Dr., Gaithersburg, MD (US) 20878

( * ) Notice: Subject to any disclaimer, the term of this patent is extended or adjusted under 35 U.S.C. 154(b) by 0 days.

(21) Appl. No.: 08/068,256

(22) Filed: May 28, 1993

(51) Int. Cl.[7] .................. A61K 31/35; A61K 31/235; A61K 31/19

(52) U.S. Cl. ............ 514/456; 514/458; 514/544; 514/570; 514/720; 514/721

(58) Field of Search .................. 514/456, 458, 514/544, 570, 720, 721

(56) References Cited

U.S. PATENT DOCUMENTS

| | | |
|---|---|---|
| 4,530,844 | 7/1985 | Smerbeck et al. . |
| 4,720,489 * | 1/1988 | Shander et al. . |
| 4,877,789 | 10/1989 | Shroot et al. . |
| 4,885,289 * | 12/1989 | Breuer et al. . |
| 5,095,007 | 3/1992 | Ahluwalia . |
| 5,096,911 | 3/1992 | Ahluwalia et al. . |
| 5,132,293 * | 7/1992 | Shander et al. . |
| 5,143,925 | 9/1992 | Shander et al. . |
| 5,189,212 | 2/1993 | Reunitz . |
| 5,271,942 | 12/1993 | Heverhagen . |
| 5,300,284 | 4/1994 | Wiechers et al. . |
| 5,364,885 | 11/1994 | Ahluwalia et al. . |
| 5,411,991 | 5/1995 | Shander et al. . |

FOREIGN PATENT DOCUMENTS

| | | |
|---|---|---|
| 0 413 528 A1 | 2/1991 | (EP) . |
| 0 532 219 A2 | 3/1993 | (EP) . |
| 0 648 488 A1 | 4/1995 | (EP) . |
| 1 458 349 | 12/1976 | (GB) . |
| 02017115 | 7/1988 | (JP) . |
| 1-96126 | 4/1989 | (JP) . |

OTHER PUBLICATIONS

Laughton et al., Inhibition of Mammalian 5–Lipoxygenase And Cyclo–Oxygenase By Flavonoids And Phenolic Dietary Additives, Biochemical Pharmacology, vol. 42, No. 9, pp. 1673–1681, 1991.

Day et al., Clinical Pharmacology Of Non–Steroidal Anti–Inflammatory Drugs, Pharmac. Ther. Vol. 33, pp. 383–433, 1987.

Higgs et al., The Mode Of Action Of Anti–Inflammatory Drugs Which Prevent The Peroxidation Of Arachidonic Acid, pp. 675–691.

Champion, Therapeutic Usage Of The Non–Steroidal Anti–Inflammatory Drugs, The Medical Journal Of Australia, vol. 149, Aug. 15, 1968.

Database WPI, Week 8441, Derwent Publications Ltd., London, GB, AN 84–254475 and JP A 59 155 314 (Rikagaku Kenkyusho) (Sep. 1984) abstract.

S.T.N., File Supplier, Karlsruhe, DE, File Chemical Abstracts, vol. 101, n. 2087 (1984).

* cited by examiner

*Primary Examiner*—Alan Siegel
(74) *Attorney, Agent, or Firm*—Fish & Richardson P.C.

(57) ABSTRACT

Mammalian hair growth is reduced by applying to the skin a composition including an inhibitor of 5-lipoxygenase.

12 Claims, No Drawings

INHIBITION OF HAIR GROWTH

The invention relates to the inhibition of hair growth.

Arachidonic acid is released from membrane lipids in response to injury or other irritation. The enzyme 5-lipoxygenase converts arachidonic acid into 5-hydroperoxyercosa-6,8,11,14-tetraenoic acid, which subsequently is converted into a family of compounds known as leukotrienes. The exact biological role of leukotrienes has not yet been determined.

It has now been found that mammalian (including human) hair growth can be inhibited by applying to the skin a composition including an inhibitor of 5-lipoxygenase in an amount effective to reduce hair growth in the applied area.

Examples of 5-lipoxygenase inhibitors that have been found effective in reducing hair growth include quercetin (3,3', 4',5,7-pentahydroxy flavone), dl-α-tocopherol, apigenin (4',5,7-trihydroxy flavone), propyl gallate, NDGA (nondihydrouaiaretic acid), and caffeic acid (3,4-dihydroxycinnamic acid). All of these compounds are known in the art and are commercially available. Other inhibitors of 5-lipoxygenase are known in the art; see, for example, Laughton et al., 42 Biochemical Pharmacology 1673 (1991).

The composition preferably includes a non-toxic dermatologically acceptable vehicle or carrier which is adapted to be spread upon the skin. Examples of suitable vehicles are acetone, alcohols, or a cream, lotion, or gel which can effectively deliver the active compound. In addition, a penetration enhancer may be added to the vehicle to further enhance the effectiveness of the formulation.

The concentration of the inhibitor in the composition may be varied over a wide range up to a saturated solution, preferably from 1 to 30% by weight or even more; the reduction of hair growth increases as the amount of inhibitor applied increases per unit area of skin. The maximum amount effectively applied is limited only by the rate at which the inhibitor penetrates the skin. Generally, the effective amounts range from 100 to 3000 micrograms or more per square centimeter of skin.

The composition should be applied to the area of the body where it is desired to inhibit hair growth. Typically, the composition can be applied to the face, particularly to the beard area of the face, i.e., the cheek, neck, upper lip, and chin. The composition can also be applied to the legs, arms, torso or armpit. The composition is particularly suitable for the treatment of hirsutism. In humans, the composition should be applied once or twice a day, or even more frequently, for at least three months to achieve a perceived reduction in hair growth.

Reduction of hair growth is demonstrated when the frequency of hair removal is reduced, or the subject perceives less hair on the treated site, or quantitatively, when the weight of hair removed by shaving (i.e., hair mass) is reduced. Male intact Golden Syrian hamsters are considered acceptable models for human beard hair growth in that they display oval shaped flank organs, one on each side, each about 8 mm. in major diameter, which grow thick black and coarse hair similar to human beard hair. These organs produce hair in response to androgens in the hamster.

To evaluate the effectiveness of a particular inhibitor, the flank organs of each of a group of hamsters are depilated by applying a thioglycolate based chemical depilatory (Surgex). To one organ of each animal 10–25 µl. of vehicle alone once a day is applied, while to the other organ of each animal an equal amount of vehicle containing the 5-lipoxygenase inhibitor is applied. After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The preferred 5-lipoxygenase inhibitors were tested according to the above procedure; the results are presented in Table 1. Vehicle A is acetone; vehicle B is 35% dipropylene glycol, 30% ethanol, 25% acetone, and 10% benzyl alcohol; vehicle C is 68% purified water, 16% ethanol (200 proof), 5% propylene glycol, 5% dipropylene glycol, 4% benzyl alcohol, and 2% propylene carbonate; vehicle D is 80% ethanol (190 proof), 17.5% purified water, 2% propylene glycol dipelargonate, and 0.5% propylene glycol; and vehicle E is a moisturizing lotion containing common cosmetic ingredients which include emulsifiers, detergents and preservatives.

TABLE 1

HAIR MASS

| Compound | Dose | Vehicle | pH | Treated (mg) | Control (mg) | Percent Inhibition |
|---|---|---|---|---|---|---|
| Quercetin | 5% | A | 6.0 | 1.100 ± .10 | 1.543 ± .10 | 27 ± 6 |
|  | 10% | B | 5.5 | 0.419 ± .07 | 2.679 ± .22 | 83 ± 4 |
| dl-α-Tocopherol | 5% | A | 5.0 | 0.400 ± .06 | 0.846 ± .10 | 49 ± 7 |
| Apigenin | 5% | C | 10.0 | 1.019 ± .22 | 2.230 ± .26 | 54 ± 9 |
|  | 10% | D | 8.0 | 0.271 ± .09 | 1.380 ± .22 | 82 ± 5 |
| Propyl gallate | 5% | D | 7.0 | 0.870 ± .15 | 2.553 ± .16 | 67 ± 5 |
| NDGA | 10% | D | 6.5 | 0.450 ± .11 | 2.391 ± .21 | 81 ± 4 |
| Caffeic acid | 5% | D | 6.0 | 1.740 ± .06 | 2.424 ± .17 | 26 ± 5 |
|  | 15% | E | 4.0 | 0.797 ± .13 | 2.148 ± .22 | 62 ± 7 |

It will be appreciated by those skilled in the art that the invention can be performed within a wide range of equivalent parameters of composition and conditions without departing from the spirit or scope of the invention or of any embodiment thereof.

What is claimed is:

1. A process of reducing mammalian hair growth, comprising
    selecting an area of skin from which reduced hair growth is desired, and
    applying to said area of skin a composition including an inhibitor of 5-lipoxygenase in an amount effective to reduce hair growth.

2. The process of claim 1, wherein said inhibitor is quercetin.

3. The process of claim 1, wherein said inhibitor is dl-α-tocopherol.

4. The process of claim 1, wherein said inhibitor is apigenin.

5. The process of claim 1, wherein said inhibitor is propyl gallate.

6. The process of claim 1, wherein said inhibitor is NDGA.

7. The process of claim 1, wherein said inhibitor is caffeic acid.

8. The process of claim 1, wherein said concentration of said inhibitor in said composition is between 1% and 30%.

9. The process of claim 1, wherein the composition is applied to the skin in an amount of from 100 to 3000 micrograms of said inhibitor per square centimeter of skin.

10. The process of claim 1, wherein the composition is applied to the skin on the face of said mammal.

11. The process of claim 1, wherein said composition further comprises a non-toxic dermatologically acceptable carrier.

12. The process of claim 1, wherein said composition is applied to the skin of a person suffering from hirsutism.

* * * * *